(12) United States Patent
Deininger et al.

(10) Patent No.: US 11,938,329 B2
(45) Date of Patent: *Mar. 26, 2024

(54) IMPLANTABLE MEDICAL DEVICES HAVING CIRCUITRY LOCATED ADJACENT TO HEADER-RELATED STRUCTURES

(71) Applicant: MEDTRONIC, INC., Minneapolis, MN (US)

(72) Inventors: Steven Deininger, Plymouth, MN (US); Jeffrey Clayton, Zimmerman, MN (US); Michael Baade, Otsego, MN (US); Anthony Chasensky, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 298 days.

This patent is subject to a terminal disclaimer.

(21) Appl. No.: 17/372,522

(22) Filed: Jul. 12, 2021

(65) Prior Publication Data

US 2021/0339029 A1 Nov. 4, 2021

Related U.S. Application Data

(63) Continuation of application No. 16/273,133, filed on Feb. 11, 2019, now Pat. No. 11,058,882.

(51) Int. Cl.
*A61N 1/375* (2006.01)
*A61N 1/36* (2006.01)
*A61N 1/05* (2006.01)

(52) U.S. Cl.
CPC ....... *A61N 1/3754* (2013.01); *A61N 1/36062* (2017.08); *A61N 1/37514* (2017.08);
(Continued)

(58) Field of Classification Search
CPC .............. A61N 1/0551; A61N 1/36062; A61N 1/36107; A61N 1/375; A61N 1/37514;
(Continued)

(56) References Cited

U.S. PATENT DOCUMENTS

| | | |
|---|---|---|
| 6,445,948 B1 | 9/2002 | Sondahl et al. |
| 7,650,191 B1 | 1/2010 | Lim et al. |

(Continued)

FOREIGN PATENT DOCUMENTS

| | | |
|---|---|---|
| EP | 0 573 532 | 12/1993 |
| EP | 0732124 | 9/1996 |
| EP | 3082952 | 10/2016 |

OTHER PUBLICATIONS

PCT/US2020/017607 Partial International Search Report dated May 27, 2020.
(Continued)

*Primary Examiner* — George Manuel
(74) *Attorney, Agent, or Firm* — WITHERS & KEYS, LLC

(57) ABSTRACT

Implantable medical devices include circuitry positioned adjacent to header-related structures, rather than having the header and related structures sitting atop the position of the circuitry within a device housing. A circuit board within the device housing may be positioned adjacently to a lead bore of the header. Feedthrough conductors may extend from the circuitry to conductors of the header while being positioned adjacently to the circuit board. Lead frame conductors may extend to the electrical connectors of the lead bores while also being adjacent to the upper portion of the circuitry. Device height may be reduced by having the circuitry be positioned adjacent to one or more of the various header-related structures.

24 Claims, 12 Drawing Sheets

(52) U.S. Cl.
CPC ........ *A61N 1/0551* (2013.01); *A61N 1/36107* (2013.01); *A61N 1/3756* (2013.01)

(58) Field of Classification Search
CPC ... A61N 1/3754; A61N 1/3756; A61N 1/3758
See application file for complete search history.

(56) References Cited

U.S. PATENT DOCUMENTS

| | | |
|---|---|---|
| 8,457,744 B2 | 6/2013 | Janzig et al. |
| 9,119,317 B2 | 8/2015 | Primavera |
| 9,393,432 B2 | 7/2016 | Wahlstrand et al. |
| 9,409,018 B2 | 8/2016 | Tourrel et al. |
| 9,707,338 B2 | 7/2017 | Seeley et al. |
| 9,950,180 B2 | 4/2018 | Janzig et al. |
| 9,956,420 B2 | 5/2018 | Kast et al. |
| 9,962,552 B2 | 5/2018 | Seeley et al. |
| 2001/0034543 A1 | 10/2001 | Hael et al. |
| 2002/0138114 A1* | 9/2002 | Gramse ................ A61N 1/3758 607/37 |
| 2007/0100385 A1 | 5/2007 | Rawat et al. |
| 2007/0232119 A1 | 10/2007 | Sprain |
| 2008/0033500 A1 | 2/2008 | Strother et al. |
| 2016/0129264 A1 | 5/2016 | Hovland et al. |
| 2016/0263384 A1 | 9/2016 | Stevenson et al. |
| 2017/0007837 A1 | 1/2017 | Dadahian et al. |

OTHER PUBLICATIONS

PCT/US2020/017607 International Search Report and Written Opinion, dated Jul. 27, 2020.

\* cited by examiner

IMPLANTABLE MEDICAL DEVICES
HAVING CIRCUITRY LOCATED ADJACENT
TO HEADER-RELATED STRUCTURES

RELATED APPLICATIONS

This present application claims priority to and is a continuation of U.S. patent application Ser. No. 16/273,133, filed Feb. 11, 2019, and entitled "IMPLANTABLE MEDICAL DEVICES HAVING CIRCUITRY LOCATED ADJACENT TO HEADER-RELATED STRUCTURES"

TECHNICAL FIELD

Implantable medical devices include circuitry that is located within a device housing while being adjacent to one or more header-related structures.

BACKGROUND

Implantable medical devices may perform various functions that require electrical circuitry to be present within a housing of the implantable medical device. For instance, an implantable medical device may provide electrical stimulation to a patient and/or may electrically sense physiological signals of the patient. The implantable medical device is implanted at a convenient location that may be at a distance from the target site where the stimulation and/or sensing should occur. An implantable medical lead may be present to carry the electrical stimulation signals and/or the sensed physiological signals between the implantable medical device and the target site.

The implantable medical device may include a header that contains one or more lead bores into which the implantable medical lead is inserted. The header typically sits atop a primary device housing. Electrical connectors present within the lead bores are electrically coupled to circuitry within the primary device housing. A feedthrough may be present at the junction of the primary device housing and the header to allow electrical conductors to exit the primary housing and enter the header without creating leaks into the primary device housing. In this manner, the electrical signals may be passed between the circuitry of the primary device housing and the electrical connectors of the header while preventing body fluids from entering the primary device housing.

While this arrangement is effective for the purposes described above, the header sitting atop the primary device housing contributes to the overall height of the device. A given device height might be less suited to certain implantation conditions and a lesser device height may therefore be more appropriate.

SUMMARY

Embodiments address issues such as these and others by providing implantable medical devices that have a circuit board that is positioned adjacent to structures related to the header, rather than the entire header and all related structures residing atop the primary device housing containing the circuit board. For instance, in some embodiments, the circuit board may be positioned adjacent to one or more of the lead bores of the header. Furthermore, in some embodiments, the circuit board may be positioned adjacent to the feedthroughs.

Embodiments provide an implantable medical device that comprises a housing and a header affixed to the housing, the header providing a first lead bore having a longitudinal centerline. The implantable medical device further comprises an electrical connector positioned within the first lead bore and a circuit board within the housing. The circuit board includes circuitry that is electrically coupled to the electrical connector, and the circuit board has a side providing a largest surface area of the circuit board. The side defines a first plane, the first lead bore being positioned such that a second plane is parallel to the longitudinal centerline of the first lead bore, intersects the first lead bore, intersects the circuit board, and is perpendicular to the first plane.

Embodiments provide an implantable medical device that comprises a housing that comprises a feedthrough wall that has a feedthrough aperture and the housing comprises an exterior wall adjacent the feedthrough wall. The implantable medical device further comprises a header affixed to the housing, the header providing a first lead bore having a longitudinal centerline. An electrical connector is positioned within the first lead bore and a circuit board is located within the housing where the circuit board includes circuitry. The feedthrough wall is positioned between the circuit board and the exterior wall and a feedthrough is positioned within the feedthrough aperture of the feedthrough wall. A feedthrough conductor is electrically coupled to the circuitry, where the feedthrough conductor extends from the circuit board and passes through the feedthrough. The feedthrough conductor has a bend on a side of the feedthrough opposite the circuit board, and the feedthrough conductor extends from the bend toward the electrical connector and between the feedthrough wall and the exterior wall. The feedthrough conductor is electrically coupled to the electrical connector.

Embodiments provide an implantable medical device that includes a housing comprising an exterior wall. The implantable medical device further comprises a circuit board within the housing where the circuit board includes circuitry. A header is affixed to the housing and borders the exterior wall such that a portion of the header lies directly adjacent to a portion of the exterior wall. The header provides a first lead bore having a longitudinal centerline, wherein the circuit board is positioned between the exterior wall and the first lead bore. An electrical connector is positioned within the first lead bore and is electrically coupled to the circuitry.

Embodiments provide an implantable medical device that includes a housing containing a circuit board that includes circuitry, the housing including a screw hole and the circuit board including a ground plane that is electrically coupled to a conductive portion. The implantable medical device further includes a header coupled to the housing, the header comprising a lead bore. The implantable medical device further includes an electrical connector within the lead bore and electrically coupled to the circuitry. A screw affixes the circuit board to the housing and electrically couples the ground plane to the housing by contacting the conductive portion while being present in the screw hole of the housing.

DETAILED DESCRIPTION

Embodiments of implantable medical devices include a circuit board that is positioned adjacent to header-related structures such as lead bores having electrical connectors, feedthrough conductors, and lead frame conductors. This allows a potentially more compact footprint than where the entire header resides atop the primary device housing so that the device may be suitable for additional implantation conditions.

Figure 1:
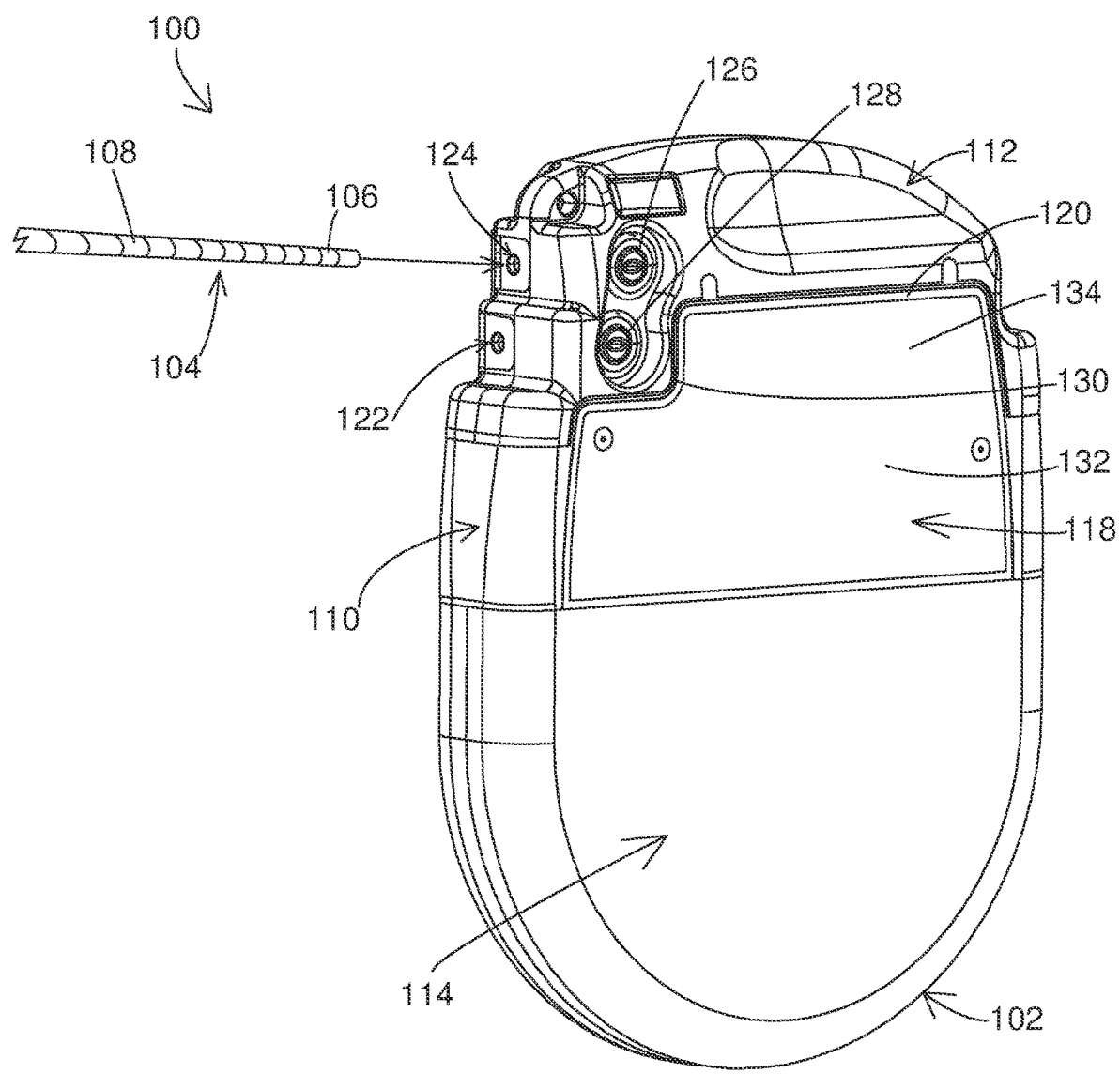
FIG. 1 shows a first perspective view of an example of an implantable medical system that includes an example of an implantable medical device with a circuit board adjacent to header-related structures.

FIG. 1 shows an example of an implantable medical system 100 that includes an implantable medical device 102 and one or more implantable medical leads 104. The implantable medical device 102 may be one of various types. For instance, the implantable medical device 102 may be an example of a neurostimulator such as those for deep brain, spinal cord, pelvic, or peripheral nerve sensing and/or stimulation. Such a device may be used to deliver electrical stimulation therapy and, in some case, also deliver a therapeutic agent, to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. In other examples, such a device may be a cardiac device used to deliver electrical stimulation to the heart.

This example of the implantable medical device 102 includes three sections, a primary device housing 110, a header body 112, and a battery enclosure 114. It will be appreciated that these sections may be modular where the header body 112 mounts to the primary device housing 110 and/or where the battery enclosure 114 mounts to the primary device housing 110. In this example, the primary device housing 110 has an exterior wall panel 118 attached thereto, and the header body 112 borders the exterior wall created by panel 118 at the junction 120 as well as a notched area 130 of the exterior wall created by 118. Alternatively, multiple of these sections may together be unitary in construction. In either case, together they form a complete device housing.

The header section 112 is affixed to or otherwise contiguous with the primary device housing 110. In one example where the header 112 is constructed of a polymer, the primary device housing 110 may include mounting barbs to which the header section 112 is molded. The header section 112 includes electrical connectors, discussed in more detail below, that are positioned within one or more lead bores 122, 124. The electrical connectors are electrically connected by feedthrough conductors or other electrical pathways to circuitry present within the primary device housing 110. When a proximal end of the lead 104 is inserted into a corresponding lead bore 122, 124, electrical contacts 106 present on the lead body 108 are electrically coupled to the electrical connectors. In this manner, signals may pass between the circuitry within the primary device housing 110 and distal electrodes located on a distal end of the lead 104, where conductors within the lead 104 carry the signals between the proximal contacts 106 and the distal electrodes.

The battery enclosure 114 is also affixed to or otherwise contiguous with the primary device housing 110. As discussed in more detail below, according to this example, the battery enclosure 114 and the primary device housing 110 may be constructed of metal such as but not limited to titanium and various grades of titanium alloys such as grade 5 and grade 23, and various grades of stainless steel such as type 316 and may be welded together at the junction with exterior wall panel 118 if not unitary. The battery enclosure 114 includes the battery as well as any isolation materials that may be included to isolate the battery from the walls of the battery enclosure section 114, especially where the walls of the battery enclosure section 114 are conductive and it is not intended for the battery enclosure section 114 to be directly electrically connected to the battery.

The primary device housing 110 houses the electrical circuitry including a circuit board and the like necessary to provide the electrical functions of the implantable medical device 102. The circuitry may include a stimulation engine capable of producing stimulation pulses. The circuitry 114 may also or alternatively include a sensing circuit capable of receiving physiological signals.

When the primary device housing 110 is metal or otherwise electrically conductive, the circuitry housed within the primary device housing 110 is separated from the walls of the primary device housing 110 such as by non-conductive regions of the circuit board. Additionally, the primary device housing 110 may include bumpers 217 that may assist in holding the circuit board 203 in position. The circuit board 203 lacks any conductive material in the areas that make contact with the bumpers 217.

As discussed above, an exterior wall panel 118 may be attached to the primary device housing 110, such as by laser seam welding. The panel 118 of this example includes two sections, a top section 134 and a lower section 132. Because a portion of the primary device housing 110 is adjacent to a portion of the header 112, rather than the entire header sitting atop the entire primary device housing, the top section 134 has the notched area 130 in order to border an area 128 of the header 112 where a set screw and related grommet of the lead bore 122 are located. Thus, even though the primary device housing 110 includes space that is adjacent the first lead bore 122, the set screw and grommet of area 128 remain accessible. The header 112 also includes an area 126 where a set screw and grommet for the lead bore 124 are located.

Figure 2:
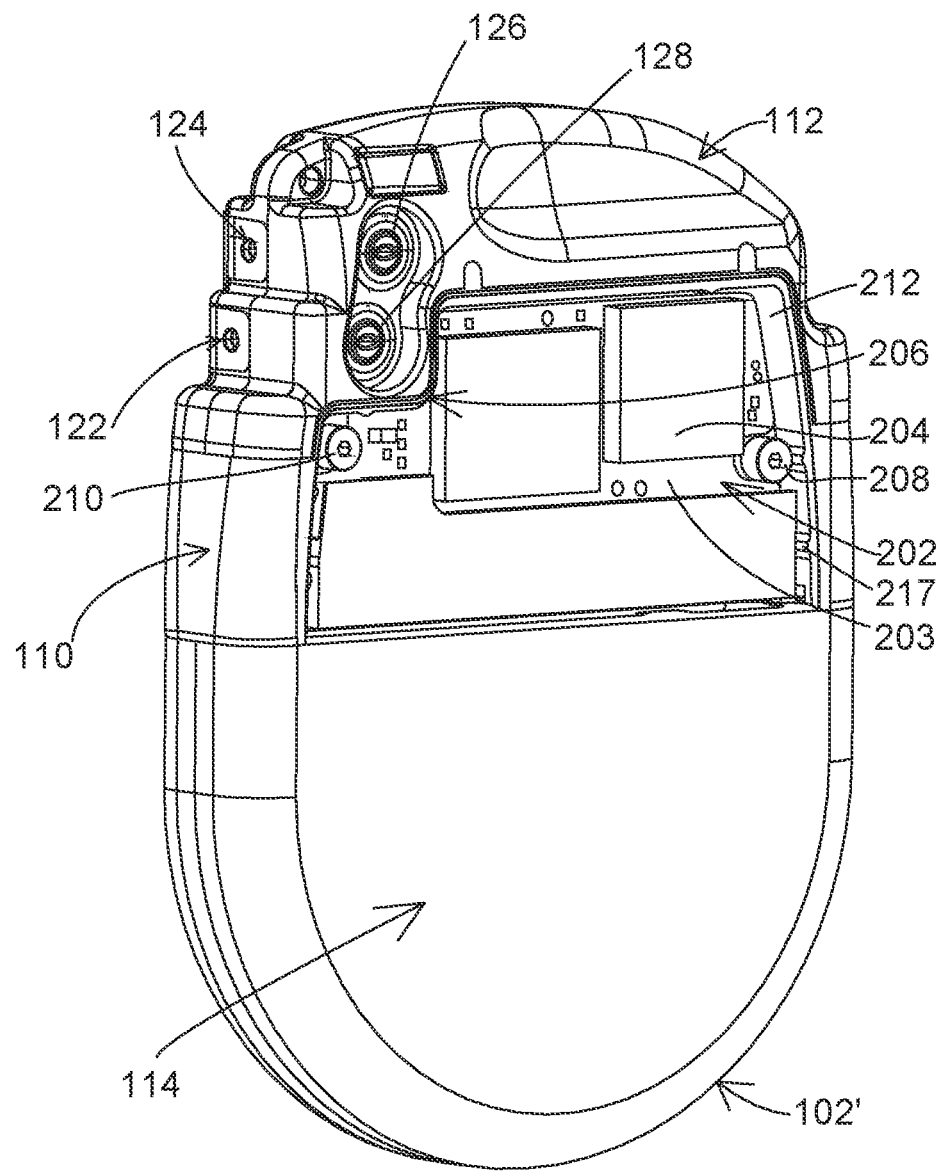
FIG. 2 shows the example of the implantable medical device with an exterior wall omitted to reveal the circuitry.
Figure 3:
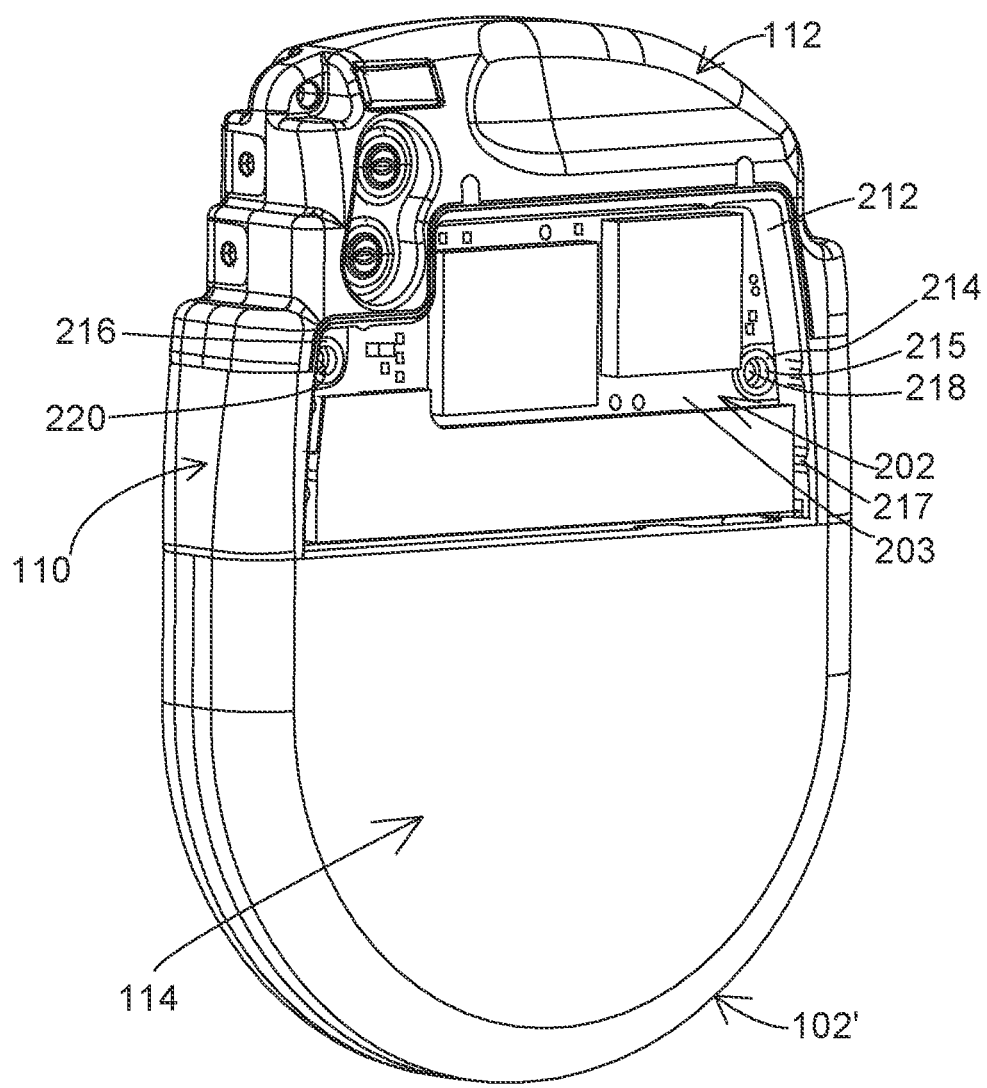
FIG. 3 shows the example of the implantable medical device with mounting screws omitted to reveal threaded holes in the device housing.

FIG. 2 shows the implantable medical device 102' where the panel 118 is omitted to reveal the circuitry 202 including various electrical components 204 present on a circuit board 203. The circuit board 203 is mounted within the primary device housing 110 in a space surrounded by a boundary wall 212 of the primary device housing 110. In this example, screws 208, 210 pass through holes in the circuit board 203 and engage threaded holes in the primary device housing 110 to secure the circuit board 203. FIG. 3 shows the implantable medical device 102' with the screws 208, 210 omitted to reveal the holes 215 of the circuit board 203 and threaded holes 218, 220 of the primary device housing 110.

To assist in maintaining the screws 208, 210 in a tightened position within the threaded holes 218, 220, the screws 208, 210 may be constructed of the same material as the primary device housing 110. The screws 208, 210 may also be prepared in the same manner such as by annealing both. By utilizing the same material and treatments, the screws 208, 210 and the housing 110 at the threaded holes 218, 220 bind against one another. Examples of this same material include but are not limited to titanium and various grades of titanium alloys such as grade 5 and grade 23, and various grades of stainless steel such as type 316.

Additionally, the screws 208, 210 may be used to electrically connect a ground plane of the circuit board 203 to the primary device housing 110. In this example, the circuit board 203 includes conductive rings 214, 216 that are electrically coupled to the ground plane, and these rings 214, 216 contact the screws 208, 210. Thus, the ground plane is electrically connected to the primary device housing 110 via the contact of the screws 208, 210 and the rings 214, 216.

Also shown in FIGS. 2 and 3, the circuit board 203 and the primary device housing 110 include a notch 206 that coincides with the notch in the panel 118 as is shown in FIG. 1. This notch 206 also provides space for the set screw and grommet for lead bore 122 within area 128 to be positioned for access while the lead bore 122 resides adjacent to the top portion of the primary device housing 110 and circuit board 203.

Figure 4:
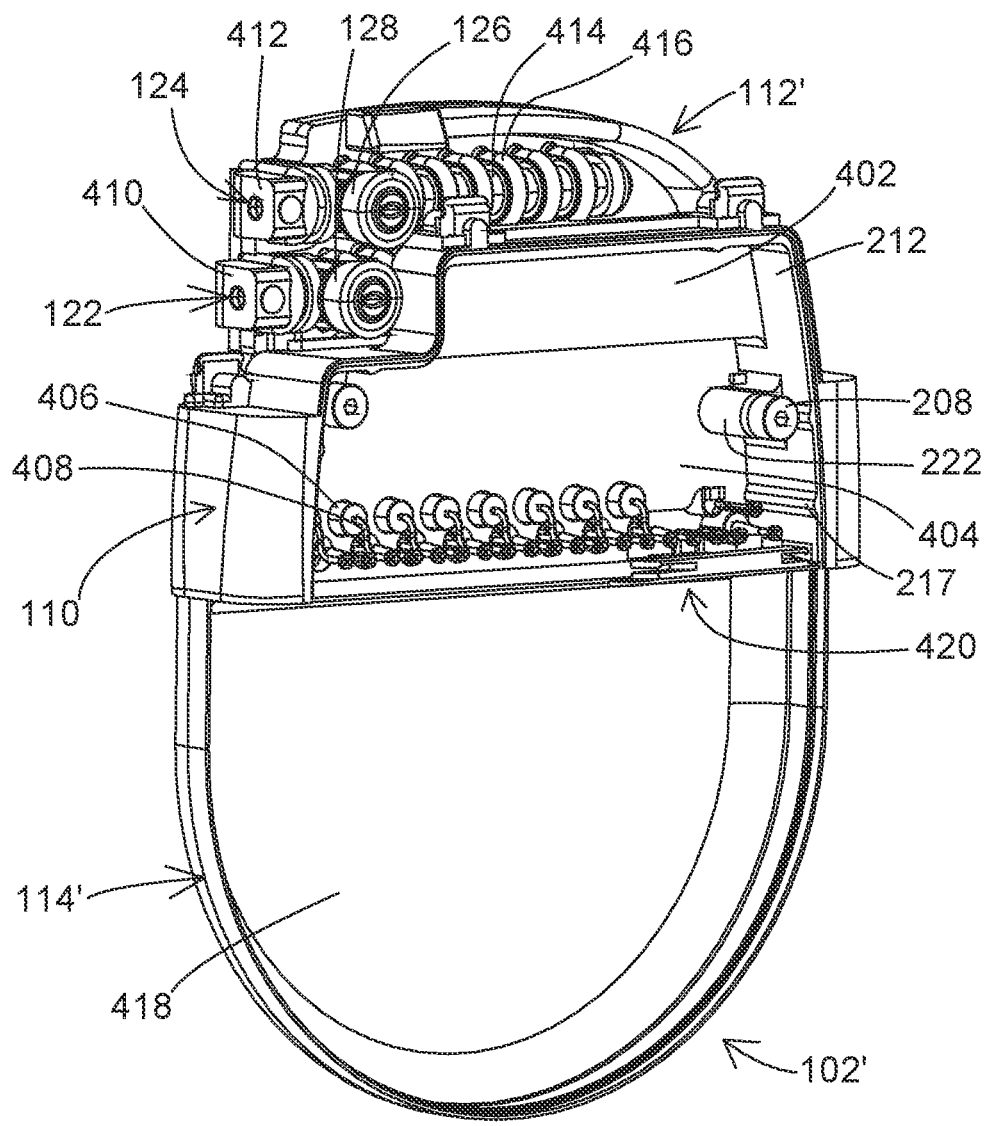
FIG. 4 shows the example of the implantable medical device with the circuit board omitted to reveal a feedthrough wall and header body omitted to reveal electrical connectors.
Figure 5:
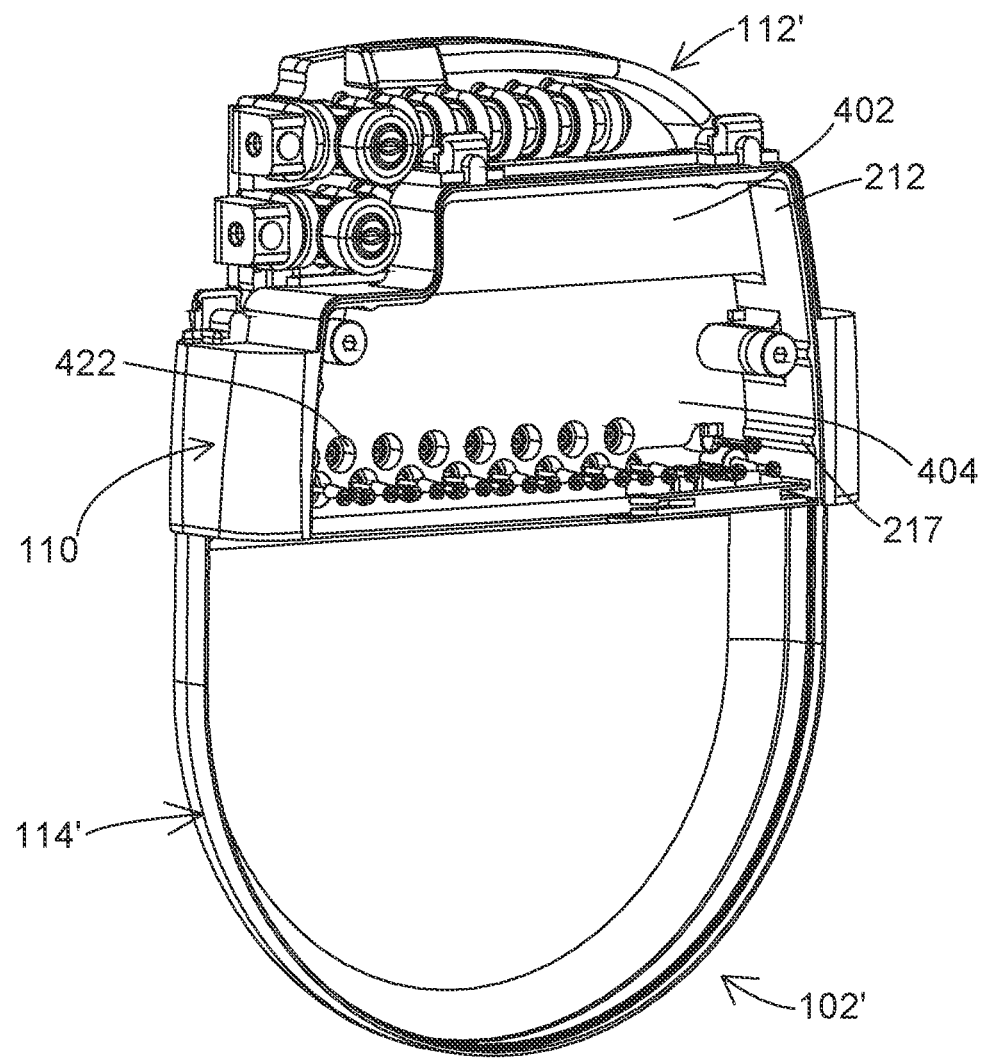
FIG. 5 shows the example of the implantable medical device with the feedthroughs omitted to reveal feedthrough holes in the feedthrough wall.

FIG. 4 shows the implantable medical device 102' with the circuit board 203 omitted to reveal an upper housing wall 402 and a lower feedthrough wall 404 that are offset from each other in this example. Feedthroughs 406 and feedthrough conductors 408 are also revealed. The feedthroughs 406 are positioned within feedthrough holes present in the lower feedthrough wall 404. These feedthrough holes 422 are shown in FIG. 5 where the feedthroughs 406 are omitted. The feedthroughs 406 provide a sealed manner of allowing the feedthrough conductors to pass from the circuit board side of the feedthrough wall 404 to the opposite side so that fluid ingress into the circuit board compartment through the feedthrough holes 422 is avoided. Additionally, the feedthroughs 406 may electrically isolate the feedthrough conductors from the primary device housing 110 for embodiments that utilize a conductive primary device housing 110.

Also shown in FIGS. 4 and 5, the header body has been omitted to reveal the header-related structures present within the header 112'. These structures include various components present for each lead bore 122, 124 such as electrical connectors 414, lead bore seals 416, and front seals 410, 412. As can be seen in FIGS. 4 and 5, the electrical connectors 414 and seals 416 of the lower lead bore 122 are directly adjacent to the upper housing wall 402, rather than sitting atop the upper housing wall 402. As can also be seen in FIGS. 4 and 5, the offset of the lower feedthrough wall 404 from the upper housing wall 402 allows the feedthrough wall 404 and feedthroughs 406 to reside beneath the lead bores 122, 124 while the upper housing wall 402 resides adjacent to the lead bore 122.

FIGS. 4 and 5 also show that the primary device housing 110 includes integral shoulders 222. These shoulders 222 contain the threaded holes 218, 220 that the screws 208, 210 are tightened within to secure the circuit board 203 in place relative to the primary device housing 110.

Additionally, FIGS. 4 and 5 show the battery enclosure 114' where one side 418 of the enclosure remains while the other side and the battery itself are omitted. FIGS. 4 and 5 reveal that a battery connector 420 may be included in some embodiments to electrically interconnect battery terminals to power terminals on the circuit board 203. This allows the battery to provide electrical power to the components 204 mounted to the circuit board 203 without the battery terminals being required to directly connect to the power terminals of the circuit board 203. The battery connector 420 may mount between the circuit board 203 and the battery in various ways.

Figure 6:
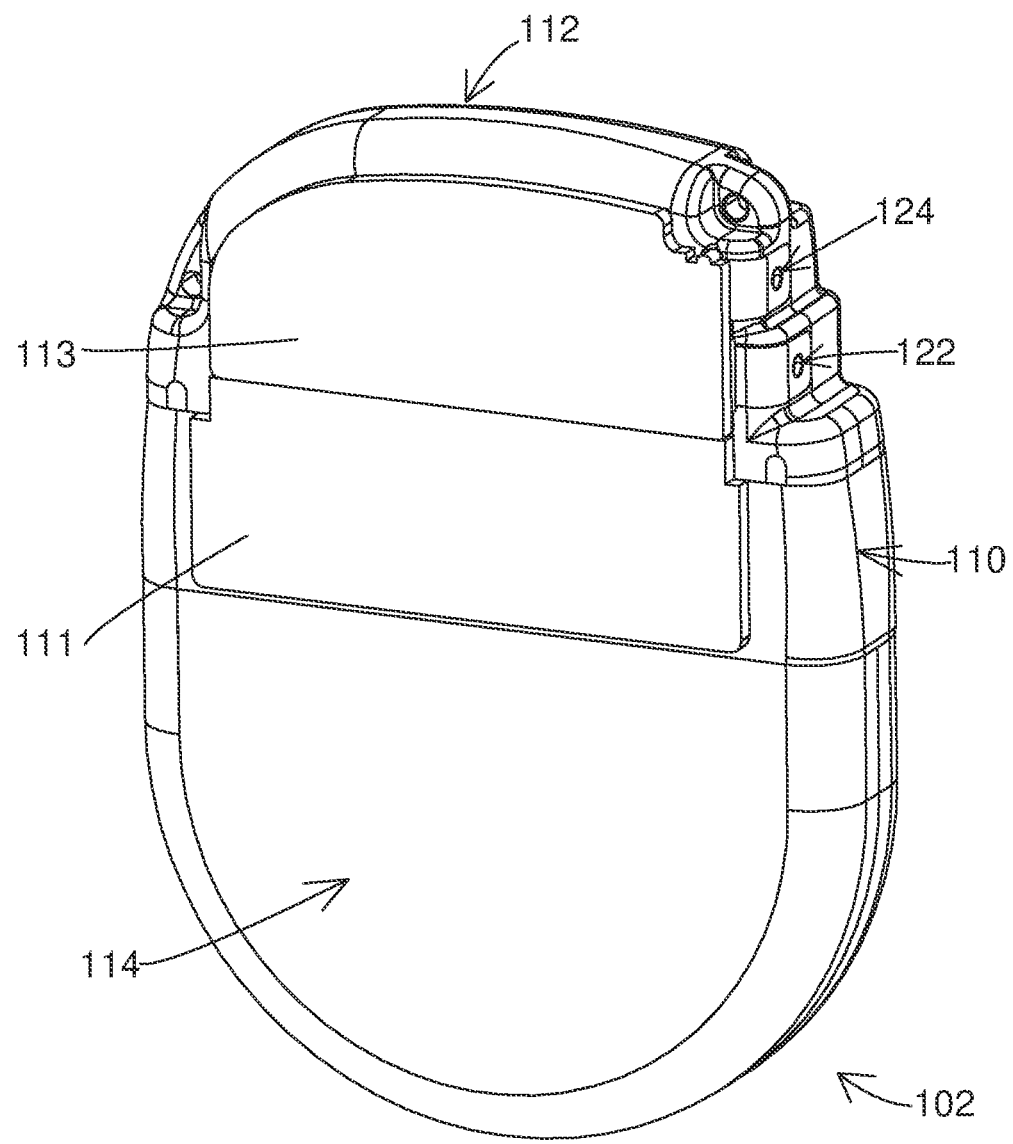
FIG. 6 shows a second perspective view of the example of the implantable medical device from the opposite side as FIG. 1.
Figure 7:
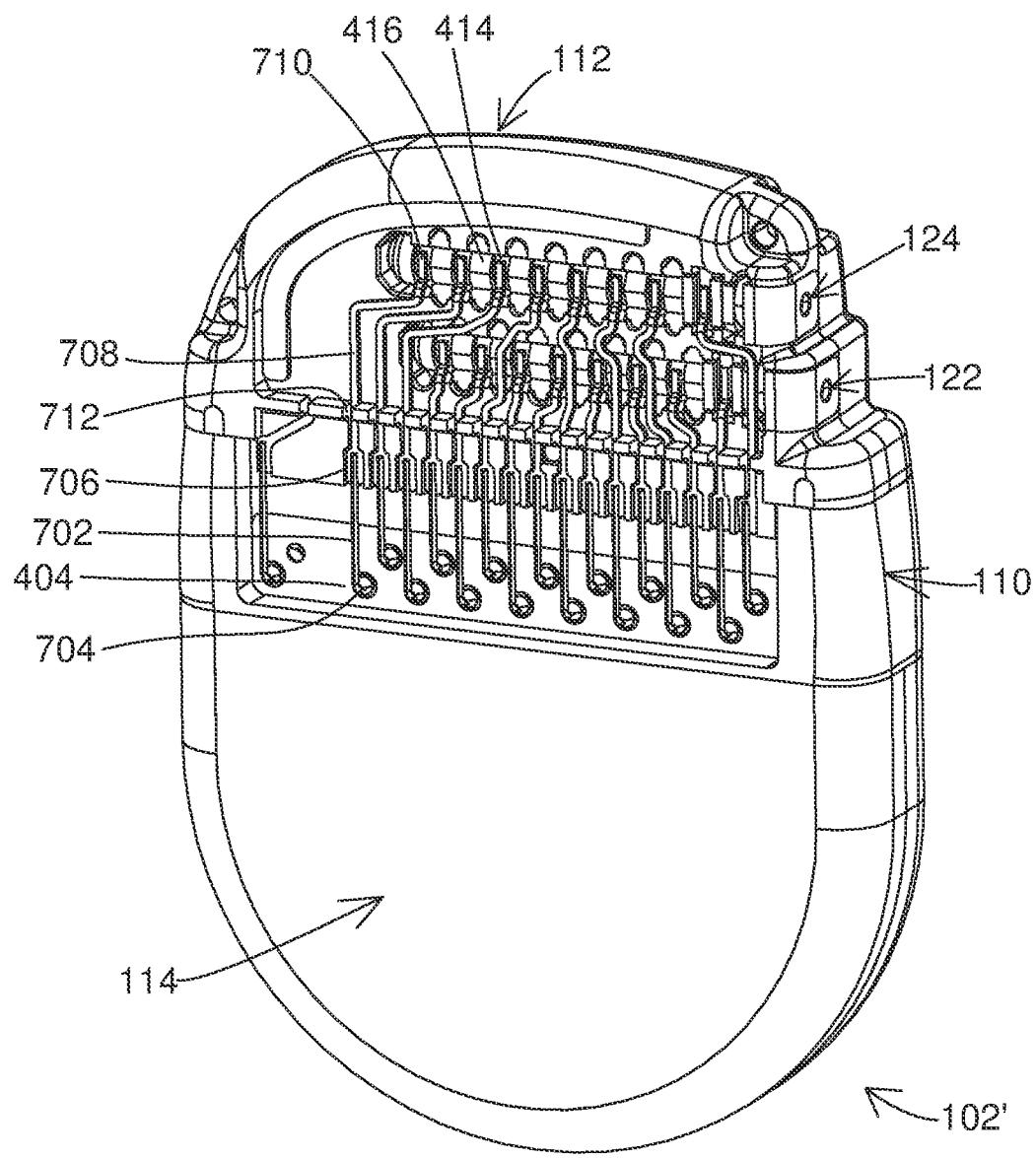
FIG. 7 shows the example of the implantable medical device with a second exterior wall and an exterior header wall omitted to reveal feedthrough conductors and lead frame conductors.

FIG. 6 shows an opposite side of the implantable medical device 102. In this example, there is an exterior wall 111 present on this side of the primary device housing 110. In this example, there is also an exterior header wall 113 on this side of the header 112. As can be seen in FIG. 7 where these exterior wall panels 111, 113 have been omitted, the extra-feedthrough portion 702 of feedthrough conductors 408 can be seen. Upon exiting the feedthrough 406, the feedthrough conductor portion 702 makes a bend 704 to then extend upward toward lead frame conductor pads 706 where they are attached to form an electrical coupling. This bend may be said to be on a side of the feedthrough 406 that is opposite the circuit board 203 since the feedthrough conductor 702 enters the feedthrough 406 on the feedthrough side that is closest to the circuit board 203 and exits the other side (i.e., the "opposite side") of feedthrough 406 before it makes the bend.

Lead frame conductors 708 extend from the lead frame conductor pads 706 to the electrical connectors 414 of the lead bores 122, 124 where they are attached via a bond 710 such as a weld. The lead frame conductors 708 carry the electrical signals between the feedthrough conductors 408 (FIG. 4) and the electrical connectors 414. The header body 112 of this example includes slots 712 that receive each of the lead frame conductors 708. As the lead frame conductors 708 are positioned adjacently to the lead bore 122, the lead frame conductors 708 are therefore also positioned adjacently to the upper portion of the circuitry 202 (FIG. 3) including the upper portion of the circuit board 203 with the electrical connectors 414 and seals 416 of the lead bore 122 being positioned between the lead frame conductors 708 and the upper housing wall 402 (FIG. 5) and circuitry 202.

During construction of the implantable medical device 102, once the connections of the lead frame conductors 708 have been made to the feedthrough conductors 702 at the pads 706 and to the electrical connectors 414 via the bonds 710, the panels 111, 113 forming exterior walls of the primary device housing 110 and header 112, respectively, may be added. One manner of doing so is to utilize a non-conductive material such as liquid silicone rubber that can fill in the space around the feedthrough conductors 702 and lead frame conductors 708 while also forming the exterior walls of panels 111, 113. Even when added as two separate exterior walls 111, 113, the two exterior panels 111, 113 may be bonded together and therefore appear as a single exterior panel.

Rather than adding the exterior wall panels at the same stage of manufacturing, the exterior wall panels 111, 113 may be added in stages, where the exterior wall panel 111 is added once the feedthrough conductor 702 is bonded to the lead frame conductor 708. Then the exterior wall panel 113 may be added at a later time once the lead frame conductor is bonded to the electrical connector 414. As another alternative, the exterior header wall panel 113 may be added to the header 112 prior to the header 112 being attached to the primary device housing 110. However, where the exterior panels are being added at the same stage, a single panel may be created as panels 111, 113 rather than two separate panels as shown in FIG. 6.

Figure 8:
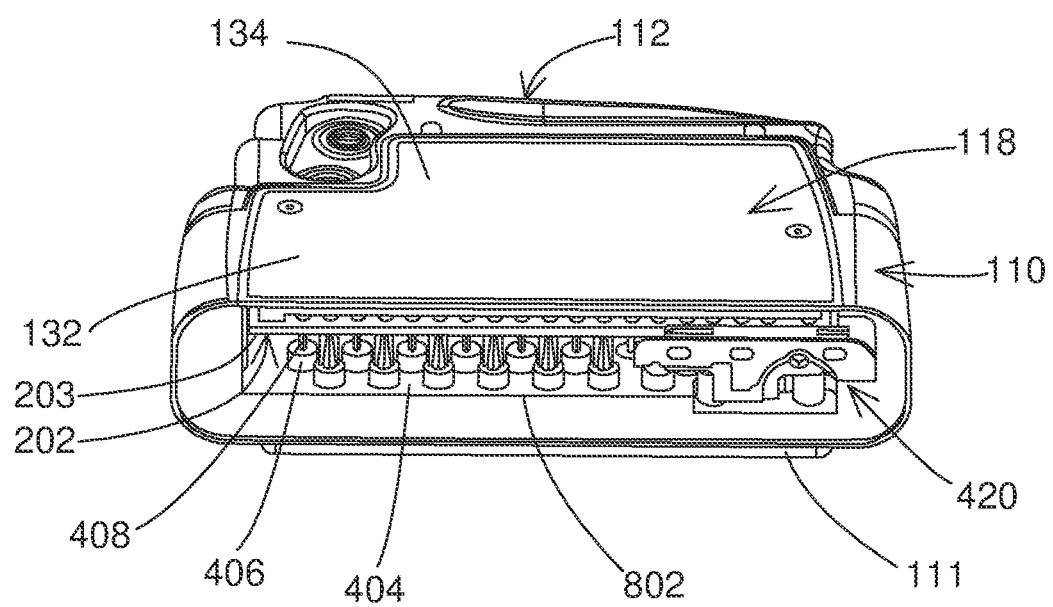
FIG. 8 shows a bottom perspective view with a battery module omitted to reveal the relative positions of the first and second exterior walls, the feedthrough wall, and the circuit board.

FIG. 8 shows a bottom perspective view of the primary device housing 110 to illustrate the position of the various components of the implantable medical device 102. In this view, it can be seen that the order of components from back to front include the panel 111, the feedthrough wall 404, the circuitry 202 including the circuit board 203, and the exterior wall panel 118. This arrangement of components is further discussed below in relation to FIG. 12. FIG. 8 also shows the battery connector 420 which resides beneath the feedthroughs 406.

Figure 9:
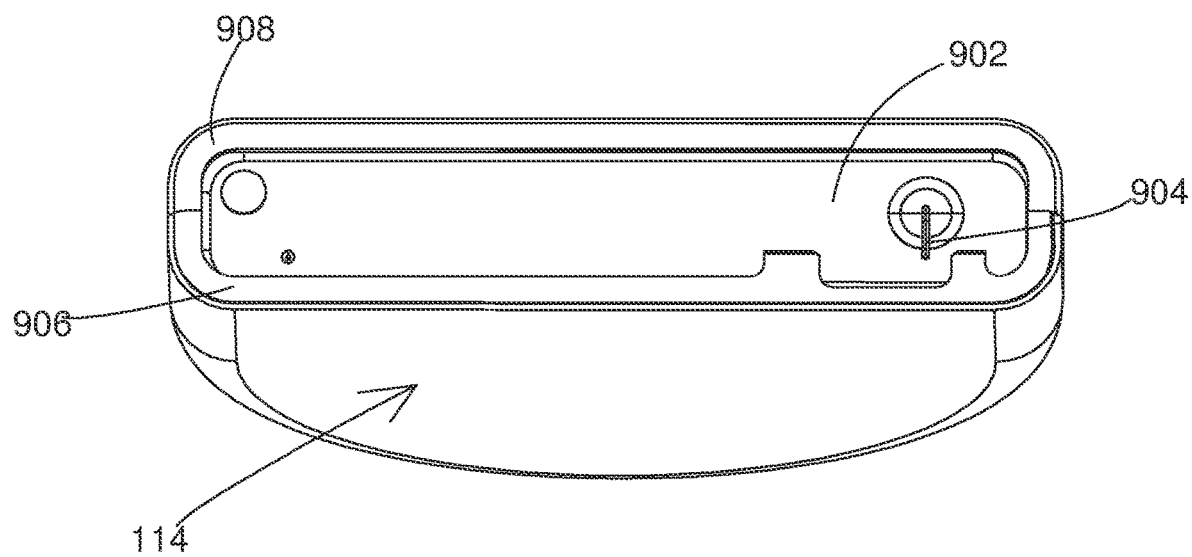
FIG. 9 shows a top perspective view of the battery module.

FIG. 9 shows a top perspective view of the battery enclosure 114. The battery enclosure 114 of this example includes a battery 902 positioned between two shells 906, 908 that are seam welded together. The battery includes a battery terminal 904 that connects to the batter connector 420. The outer casing of the battery 902 may also act as a battery terminal and may connect to the battery connector 420. Additionally, where the battery enclosure 114 is conductive but is not intended to be directly electrically connected to the battery 902, then the battery 902 may be covered with a non-conductive material, such as a polymer cup, that isolates the battery 902 from the shells 906, 908. The shells 906, 908 are attached to the bottom of the primary device housing 110 such as by a laser seam weld.

Figure 10:
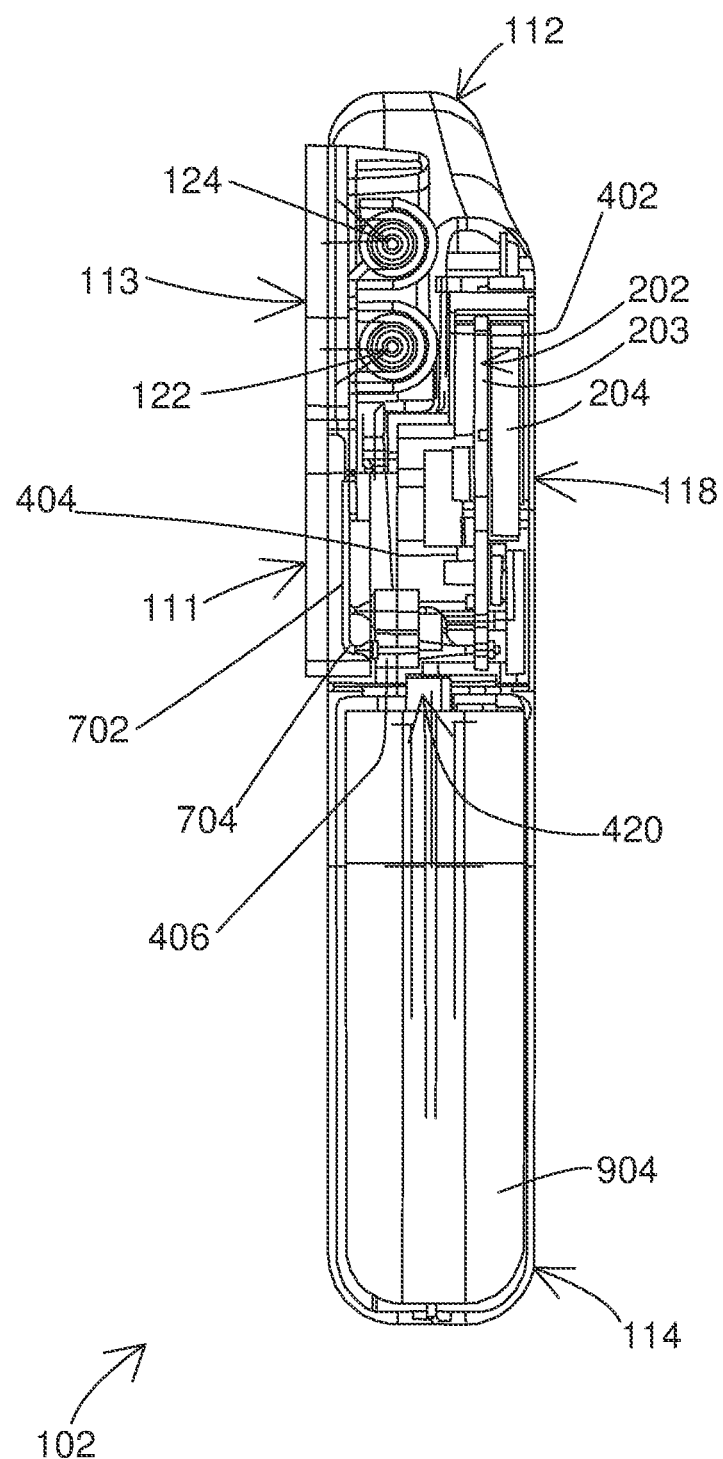
FIG. 10 shows a cross-sectional that reveals the relative position of the lead bores, the first and second exterior walls, the header wall, and the circuit board.

FIG. 10 is a cross-sectional view of the implantable medical device where the view is looking through the lead bores 122, 124 from back to front. This view illustrates the position of the various components in this example of the implantable medical device 102. Here it can be seen that from left to right there is the panel 111 providing the exterior wall; the feedthrough conductor 702; the lower feedthrough wall 404 positioned directly beneath the lead bores 122, 124; the circuitry 202 including the circuit board 203 and electrical components 204; and then the exterior wall panel 118. Here it can also be seen that from left to right there is the panel 113; the lead bores 122, 124; the upper housing wall 402; the circuitry 202 including the circuit board 203 and the electrical components 204; and the exterior wall panel 118.

It can be appreciated from FIG. 10 that the device height has been reduced compared to a conventional implantable medical device that places the lead bores atop the primary device housing. Specifically, the device height in this example is reduced at least as a result of the lead bore 122 being adjacent to an upper portion of the circuitry 202 including an upper portion of the circuit board 203, rather than both lead bores 122, 124 being positioned above the circuitry 202.

Figure 11:
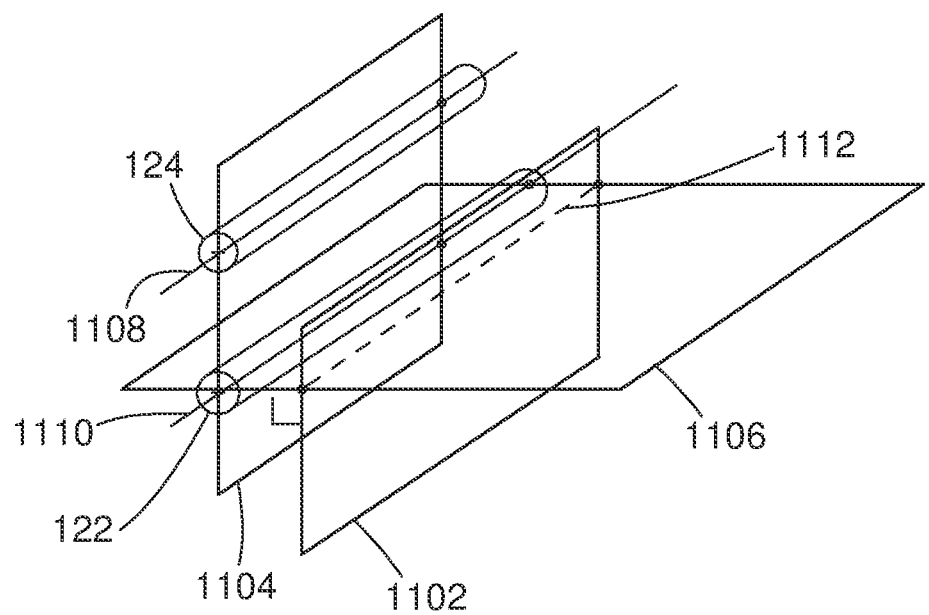
FIG. 11 is an illustration of the relative positions of a first plane formed by the circuit board of the implantable medical device as well a second plane, a third plane, and first and second lead bores.

FIG. 11 shows geometric relationships that may be utilized by various embodiments of the implantable medical device 102, including the example as shown in FIG. 10 to position the lead bore adjacent to the primary device housing 110 and related components. A first plane 1102 is formed by a side of the circuit board 203. A second plane 1106 is not necessarily defined by any particular object within the implantable medical device 102 but instead is introduced to provide the relationships of components. The second plane provides constraints by being perpendicular to the first plane 1102 while also intersecting both the first plane 1102 as shown at 1112 and also intersecting the lead bore 122. The second plane 1106 is also parallel to a longitudinal centerline 1110 of the lead bore 122. For some embodiments the second plane 1106 may provide further constraints such as by bisecting the lead bore 122 through the longitudinal centerline and/or by being parallel to the longitudinal centerline 1108 of the second lead bore 124.

FIG. 11 further illustrates a third plane 1104. Like the second plane 1106, the third plane 1104 is not necessarily defined by any particular object within the implantable medical device 102 but instead is introduced to provide the relationships of components. The third plane 1104 is parallel to the first plane 1102 while passing through the centerline of the first lead bore 122 and the second lead bore 124. For some embodiments the third plane 1104 may provide further constraints such as by being parallel to the lower feedthrough wall 404, being defined by a surface of the lower feedthrough wall 404, and/or being coplanar with a surface of the lower feedthrough wall 404 while bisecting the lower feedthrough wall 404. In still other embodiments, the third plane 1104 only passes through the centerline of either the first lead bore 122 or the second lead bore 124 because the centerlines of the two lead bores are offset somewhat from one another. In this case, a fourth plane (not shown) passes through the centerline of the other one of the first or second lead bore and is parallel to the first plane 1102 and third plane 1104. For some embodiments the fourth plane may provide further constraints such as by being parallel to the lower feedthrough wall 404, being defined by a surface of the lower feedthrough wall 404, and/or being coplanar with a surface of the lower feedthrough wall 404 while bisecting the lower feedthrough wall 404.

Figure 12:
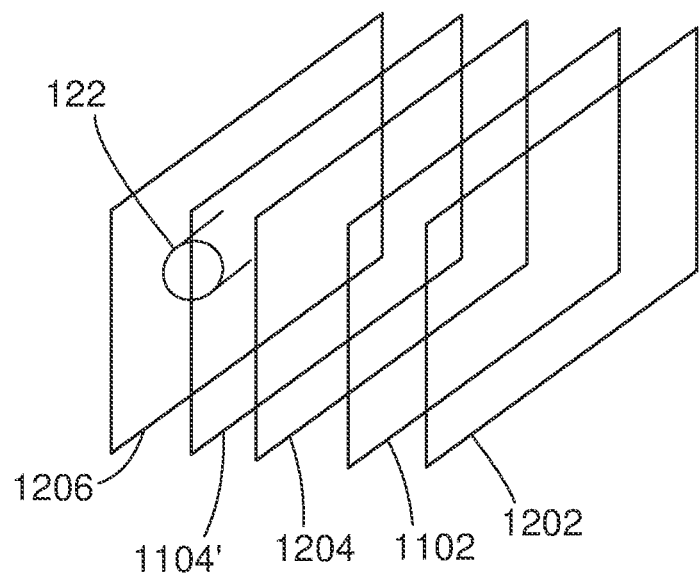
FIG. 12 is an illustration of the relative positions of the first plane formed by the circuit board, the third plane, and planes formed by the first and second exterior walls and the feedthrough wall.

FIG. 12 also shows geometric relationships that may be utilized by various embodiments of the implantable medical device 102 including the example as shown in FIG. 8 to position the header-related structures including the lead bore adjacent to the primary device housing 110 and related components. FIG. 12 shows the first plane 1102 and the third plane 1104' as discussed above in FIG. 11, including the third plane 1104' intersecting the lead bore 122. In this specific example, the third plane 1104' represents a plane established by the lower feedthrough wall 404. A plane 1202 defined by the outer surface of the exterior wall panel 118 is the right-most plane. To the left of plane 1202 resides the first plane 1102 of the circuit board 203 and then a plane 1204 defined by the outer surface of the upper housing wall 402. To the left of plane 1204 resides the third plane 1104' and then a plane 1206 established by the outer surface of the exterior wall panels 111, 113. Any combination or all of these planes of FIG. 12 may be parallel to each other.

From FIGS. 10 and 12, various observations can be made. For instance, it can be seen that the lead bore 122 is positioned between the circuit board 203 and the wall established by panels 111, 113. It can be seen that the circuit board 203 is positioned between the first lead bore 122 and the wall established by panel 118. It can further be seen that the lower feedthrough wall 404 is positioned between the circuit board 203 and the exterior wall established by the panels 111, 113 such that this exterior wall is adjacent lower feedthrough wall 404. It can further be seen that the feedthrough conductors are present between the lower feedthrough wall 404 and the wall established by the panels 111, 113.

While embodiments have been particularly shown and described, it will be understood by those skilled in the art that various other changes in the form and details may be made therein without departing from the spirit and scope of the invention.

What is claimed is:

1. An implantable medical device, comprising:
   a housing;
   a header affixed to the housing, the header providing a first lead bore and a second lead bore, the first lead bore and the second lead bore having a longitudinal centerline that are parallel and separated in a first dimension;
   an electrical connector positioned within the first lead bore;
   a circuit board within the housing, the circuit board including circuitry that is electrically coupled to the electrical connector, the circuit board having a side providing a largest surface area of the circuit board, the side defining a first plane, the first lead bore being positioned such that a second plane is parallel to the longitudinal centerline of the first, intersects the first lead bore but not the second lead bore, intersects the circuit board, and is perpendicular to the first plane.

2. The implantable medical device of claim 1, wherein the second plane is parallel to the longitudinal centerline of the second lead bore.

3. The implantable medical device of claim 2, wherein a third plane is parallel to the first plane and passes through the centerline of the first lead bore and through the centerline of the second lead bore.

4. The implantable medical device of claim 1, wherein the housing comprises a first wall that is parallel to the first plane and a second wall that is parallel to the first plane, wherein the first lead bore is positioned between the circuit board and the first wall and the circuit board is positioned between the first lead bore and the second wall.

5. The implantable medical device of claim 1, wherein the housing comprises a feedthrough wall that has a feedthrough aperture and the housing comprises an exterior wall adjacent the feedthrough wall such that the feedthrough wall is positioned between the circuit board and the exterior wall, the implantable medical device further comprising:
   a feedthrough positioned within the feedthrough aperture of the feedthrough wall; and
   a feedthrough conductor electrically coupled to the circuitry, the feedthrough conductor extending from the side of the circuit board and passing through the feedthrough, the feedthrough conductor having a bend on a side of the feedthrough opposite the circuit board, the feedthrough conductor extending from the bend toward the electrical connector and between the feedthrough wall and the exterior wall, the feedthrough conductor being electrically coupled to the electrical connector.

6. The implantable medical device of claim 1, wherein the housing comprises threaded holes, the implantable medical device further comprising screws passing through the circuit board and engaging the threaded holes.

7. The implantable medical device of claim 6, wherein the screws and the housing providing the threaded holes are a same material.

8. An implantable medical device, comprising:
   a housing that comprises an upper wall and a feedthrough wall that has a feedthrough aperture and the housing comprises an exterior wall adjacent the feedthrough wall, the upper wall and the feedthrough wall being offset in a first dimension;
   a header affixed to the housing, the header providing a first lead bore having a longitudinal centerline, the first lead bore being adjacent the upper wall in the first dimension;
   an electrical connector positioned within the first lead bore;
   a circuit board within the housing, the circuit board including circuitry, the feedthrough wall being positioned between the circuit board and the exterior wall;
   a feedthrough positioned within the feedthrough aperture of the feedthrough wall; and
   a feedthrough conductor electrically coupled to the circuitry, the feedthrough conductor extending from the circuit board and passing through the feedthrough, the feedthrough conductor having a bend on a side of the feedthrough opposite the circuit board, the feedthrough conductor extending from the bend toward the electrical connector and between the feedthrough wall and the exterior wall, the feedthrough conductor being electrically coupled to the electrical connector.

9. The implantable medical device of claim 8, wherein the circuit board has a side providing a largest surface area of the circuit board, the side defining a first plane.

10. The implantable medical device of claim 9, wherein the feedthrough wall and the exterior wall define planes that are parallel to the first plane.

11. The implantable medical device of claim 9, the first lead bore being positioned such that a second plane is parallel to the longitudinal centerline of the first lead bore, intersects the first lead bore, intersects the circuit board, and is perpendicular to the first plane.

12. The implantable medical device of claim 11, wherein the header provides a second lead bore having a longitudinal centerline, the second lead bore being separated from the first lead bore in a second dimension that is perpendicular to the first dimension, and wherein the second plane is parallel to the longitudinal centerline of the second lead bore.

13. The implantable medical device of claim 12, wherein a third plane is parallel to the first plane and passes through the centerline of the first lead bore and through the centerline of the second lead bore.

14. The implantable medical device of claim 11, wherein the housing comprises a second exterior wall and an upper housing wall, wherein the header comprises a header wall, and wherein the first lead bore is positioned between the upper housing wall and the header wall and the circuit board is positioned between the upper housing wall and the second exterior wall.

15. An implantable medical device, comprising:
   a housing comprising an exterior wall;
   a circuit board within the housing, the circuit board including circuitry;
   a header affixed to the housing and bordering the exterior wall such that a portion of the header lies directly adjacent to a portion of the exterior wall, the header providing a first lead bore and a second lead bore, the first lead bore and the second lead bore each having a longitudinal centerline, wherein the circuit board is positioned between the exterior wall and the first lead bore and not between the exterior wall and the second lead bore;
   a first electrical connector that is positioned within the first lead bore and that is electrically coupled to the circuitry; and a second electrical connector that is positioned within the second lead bore and that is electrically coupled to the circuitry.

16. The implantable medical device of claim 15, wherein the circuit board has a side providing a largest surface area of the circuit board, the side defining a first plane, the first lead bore being positioned such that a second plane is parallel to the longitudinal centerline of the first lead bore, intersects the first lead bore, intersects the circuit board, and is perpendicular to the first plane.

17. The implantable medical device of claim 16, wherein the second plane is parallel to the longitudinal centerline of the second lead bore.

18. The implantable medical device of claim 17, wherein a third plane is parallel to the first plane and passes through the centerline of the first lead bore and through the centerline of the second lead bore.

19. The implantable medical device of claim 16, wherein the header comprises a first wall that is parallel to the first plane and the housing comprises a second wall that is parallel to the first plane, wherein the first lead bore is positioned between the circuit board and the first wall and the circuit board is positioned between the first lead bore and the second wall.

20. The implantable medical device of claim 16, wherein the housing comprises a feedthrough wall that has a feedthrough aperture and the housing comprises an exterior wall adjacent the feedthrough wall such that the feedthrough wall is positioned between the circuit board and the exterior wall, the implantable medical device further comprising:
   a feedthrough positioned within the feedthrough aperture of the feedthrough wall; and
   a feedthrough conductor electrically coupled to the circuitry, the feedthrough conductor extending from the side of the circuit board and passing through the feedthrough, the feedthrough conductor having a bend on a side of the feedthrough opposite the circuit board, the feedthrough conductor extending from the bend toward the electrical connector and between the feedthrough wall and the exterior wall, the feedthrough conductor being electrically coupled to the first electrical connector.

21. The implantable medical device of claim 15, wherein the housing comprises threaded holes, the implantable medical device further comprising screws passing through the circuit board and engaging the threaded holes.

22. The implantable medical device of claim 21, wherein the screws and the housing providing the threaded holes are a same material.

23. The implantable medical device of claim 15, wherein the circuit board includes a ground plane that is electrically coupled to a conductive portion of the circuit board, wherein the housing includes a screw hole, and the implantable medical device further comprising a screw that affixes the circuit board to the housing and electrically couples the ground plane to the housing by contacting the conductive portion while being present in the screw hole of the housing.

24. An implantable medical device, comprising:
   a housing containing a circuit board that includes circuitry, the circuit board defining a first plane, the housing including a screw hole defining an axis perpendicular to the first plane, and the circuit board including a ground plane that is electrically coupled to a conductive portion of the circuit board;
   a header coupled to the housing, the header comprising a lead bore;
   an electrical connector within the lead bore and electrically coupled to the circuitry; and
   a screw that affixes the circuit board to the housing and electrically couples the ground plane to the housing by contacting the conductive portion while being present in the screw hole of the housing.

* * * * *